(12) United States Patent
Ansmann et al.

(10) Patent No.: US 6,469,211 B2
(45) Date of Patent: Oct. 22, 2002

(54) HYDROGENATION OF NITRILES OVER RANEY CATALYSTS

(75) Inventors: Andreas Ansmann, Wiesloch; Christoph Benisch, Eppelheim; Frank Funke, Frankenthal; Frank Ohlbach, Düsseldorf; Martin Merger, Frankenthal, all of (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 09/987,243

(22) Filed: Nov. 14, 2001

(65) Prior Publication Data

US 2002/0058842 A1 May 16, 2002

(30) Foreign Application Priority Data

Nov. 16, 2000 (DE) .......................................... 100 56 840

(51) Int. Cl.$^7$ ............................................. C07C 209/48
(52) U.S. Cl. ........................ 564/415; 564/491; 564/492; 564/493
(58) Field of Search ................................ 564/415, 491, 564/492, 493

(56) References Cited

U.S. PATENT DOCUMENTS 4,739,120 A * 4/1988 Zuckerman .................. 564/385

OTHER PUBLICATIONS

Database CAPLUS on STN, Acc. No. 1973:466203, Habermann et al., DE 2159736, (abstract).*

* cited by examiner

*Primary Examiner*—Brian J. Davis
(74) *Attorney, Agent, or Firm*—Keil & Weinkauf

(57) ABSTRACT

In a process for the continuous hydrogenation of nitrites to primary amines in the liquid phase over a suspended, activated Raney catalyst based on an alloy of aluminum and at least one transition metal selected from the group consisting of iron, cobalt and nickel, and, if desired, one or more further transition metals selected from the group consisting of titanium, zirconium, chromium and manganese, the hydrogenation is carried out in the absence of ammonia and basic alkali metal compounds or alkaline earth metal compounds.

9 Claims, No Drawings

HYDROGENATION OF NITRILES OVER RANEY CATALYSTS

The present invention relates to a process for hydrogenating nitrites to primary amines over an activated Raney catalyst.

It is known that nitriles and iminonitriles can be hydrogenated in the liquid phase over Raney catalysts.

EP-A-0 382 508 describes the semicontinuous hydrogenation of polynitriles in the liquid phase over Raney cobalt catalysts in the presence of anhydrous ammonia.

U.S. Pat. No. 5,869,653 describes a continuous process for hydrogenating nitrites over Raney cobalt catalysts in the absence of ammonia, which is carried out in the presence of catalytic amounts of lithium hydroxide and water.

U.S. Pat. No. 4,895,994 discloses a Raney catalyst having a BET surface area of from 20 to 80 $m^2/g$ and a proportion of macropores of from 0.01 to 70% by volume, based on the total pore volume, which is produced by mixing the Raney alloy with a high molecular weight polymer, shaping the mixture to form a shaped body, calcining the composition firstly at from 300 to 700° C. and subsequently at from 850 to 1200° C. in the presence of oxygen and leaching aluminum from the calcined shaped body by treatment with 6 N NaOH at from 90 to 100° C. The catalyst which has been activated in this way is subsequently washed repeatedly with water until the pH of the washings is <9. The Raney catalyst is used, inter alia, for hydrogenating nitrites to amines.

EP-A-0 842 699 discloses a process for producing an activated, metal powder-free, macroporous fixed-bed metal catalyst of the Raney type based on an alloy of aluminum and at least one metal of transition group VIII of the Periodic Table, which comprises the steps (1) preparing a kneadable composition comprising the alloy, a shaping aid, water and a pore former, (2) shaping the kneadable composition to give a shaped body, (3) calcining the shaped body and (4) treating the calcined shaped body with an alkali metal hydroxide. After treatment of the shaped body with alkali metal hydroxide, the activated catalyst is washed with water until the pH of the washings has dropped to 7.5. The catalyst obtained in this way has a macropore content of more than 80% by volume. The catalyst is used for hydrogenating nitrites to primary amines.

Such a process is also disclosed in DE-A 44 46 907, in which polyvinyl alcohol and water or stearic acid are used as auxiliaries.

A disadvantage of the semicontinuous or continuous processes of the prior art is that they are carried out either in the presence of ammonia as solvent or in the presence of basic alkali metal compounds such as LiOH. The hydrogenation in the presence of ammonia brings with it an additional engineering outlay associated with the separation, work-up and recirculation of the ammonia. Basic alkali metal compounds are corrosive and their use therefore likewise requires additional engineering outlay.

It is an object of the present invention to provide a simple-to-carry out process for the gentle hydrogenation of nitrites, in particular to provide a process of this type which displays high selectivity in respect of the formation of primary amines and in which secondary reactions such as dissociation of the nitrites are avoided.

We have found that this object is achieved by a process for the continuous hydrogenation of nitrites to primary amines in the liquid phase over a suspended, activated Raney catalyst based on an alloy of aluminum and at least one transition metal selected from the group consisting of iron, cobalt and nickel, and, if desired, one or more further transition metals selected from the group consisting of titanium, zirconium, chromium and manganese, wherein the hydrogenation is carried out in the absence of ammonia and basic alkali metal compounds or alkaline earth metal compounds.

Catalysts which are preferably used in the process of the present invention are produced on the basis of an alloy of aluminum and a solid solution of nickel in cobalt or cobalt in nickel comprising 0.05–50% by weight of the dissolved metal and, if desired, from 0.05 to 5% by weight of the further transition metal or metals.

The catalysts are preferably activated by (a) treatment with aqueous alkali metal hydroxide solution, if desired (b) rinsing the catalyst with aqueous alkali metal hydroxide solution and, if desired, (c) rinsing the catalyst with water.

Preferred transition metals are nickel and cobalt; particular preference is given to solid solutions of nickel in cobalt or cobalt in nickel in which the dissolved metal is present in a concentration of from 0.05 to 50% by weight. To increase the activity and selectivity, the alloy may further comprise at least one additional transition metal selected from among titanium, zirconium, chromium and manganese as promoter, generally in concentrations of from 0.01 to 15% by weight, preferably from 0.05 to 5% by weight, based on the total amount of transition metals. The weight ratio of aluminum to transition metal is generally in the range from 30 to 70% by weight of aluminum and from 30 to 70% by weight of transition metal.

The aluminum alloy is produced in a manner known per se, for example as described in DE 21 59 736, whose contents relating to the production of alloys of aluminum and the specified transition metals are hereby incorporated by reference into the present application.

The calcined shaped bodies are, according to the present invention, activated using an alkali metal hydroxide, preferably lithium hydroxide, sodium hydroxide, potassium hydroxide or cesium hydroxide or a mixture thereof, particularly preferably using sodium hydroxide alone or in admixture with the abovementioned alkali metal hydroxides. In general, use is made of aqueous solutions of the alkali metal hydroxide, preferably aqueous sodium hydroxide solution, with the alkali metal hydroxide solution having a concentration of generally from 5 to 30% by weight, preferably from 15 to 25% by weight. The molar ratio of alkali metal hydroxide to aluminum is generally from about 1:1 to about 5:1, preferably from about 1.5:1 to about 3:1.

The activation temperature is usually from about 25° C. to about 106° C., preferably from about 45° C. to about 90° C.

The activation time depends essentially on the desired final aluminum content and is in the range from 1 to 10 hours, preferably from 2 to 5 hours. The activation procedure can also be carried out a number of times.

After the activation procedure, the shaped catalyst body can be rinsed with water. The shaped catalyst body is, after the activation, preferably rinsed firstly with aqueous alkali metal hydroxide solution and subsequently with water.

Preferably, rinsing is carried out using an aqueous solution of the alkali metal hydroxide having a concentration of generally from 5 to 30% by weight, preferably from 15 to 25% by weight. Particularly preferably, rinsing is carried out using the same alkali metal hydroxide used in the activation of the catalyst and the alkali metal hydroxide concentration of the rinsing solution is the same as that of the alkali metal hydroxide solution used for activation. Rinsing is preferably carried out at room temperature. Rinsing with alkali metal hydroxide solution can be carried out a number of times, preferably three times, with the total amount of the alkali metal hydroxide solution used being similar to that used in the activation. Only then is rinsing with water carried out, preferably until the pH of the washings is about 8.

The washed, activated shaped catalyst bodies are stored under water, preferably in a mixture of water and methanol.

According to the present invention, any nitriles can be hydrogenated to give the corresponding primary amines. Nitriles preferred for hydrogenation by the process of the present invention are extender nitriles and nitriles which can be obtained by Michael addition, having the formula (I) or (II)

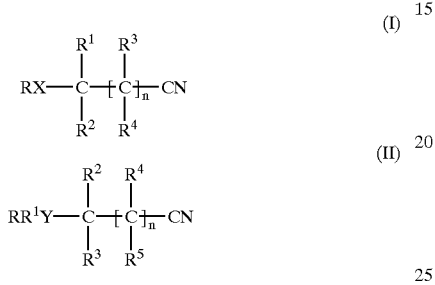

where
X is O or S,
Y is N or P,
n is 0 or 1
and
$R, R^1, R^2, R^3, R^4, R^5$ are each, independently of one another, H or a substituted or unsubstituted alkyl radical having 1–10 carbon atoms or a substituted or unsubstituted aryl radical having 6–12 carbon atoms.

Examples are iminodiacetonitrile, nitrilotriacetonitrile, ethylenediaminetetraacetonitrile, biscyanoethylpiperazine, dimethylaminopropionitrile, dimethylaminopropylaminopropionitrile and methoxypropionitrile.

Further preferred nitriles are cyclic iminonitriles and acyclic iminonitriles of the formulae (III) and (IV)

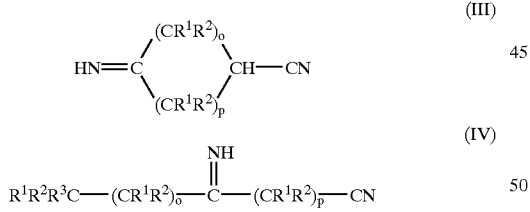

where
$R^1$, $R^2$ and $R^3$ are each, independently of one another, H or a substituted or unsubstituted alkyl radical having 1–10 carbon atoms or a substituted or unsubstituted aryl radical having 6–12 carbon atoms and
o, p are each 0, 1, 2, 3, 4 or 5.

An example is isophoronenitrilimine.

Further important nitriles and aminonitriles which can be hydrogenated by the process of the present invention are the compounds (V) to (XXXII) below:

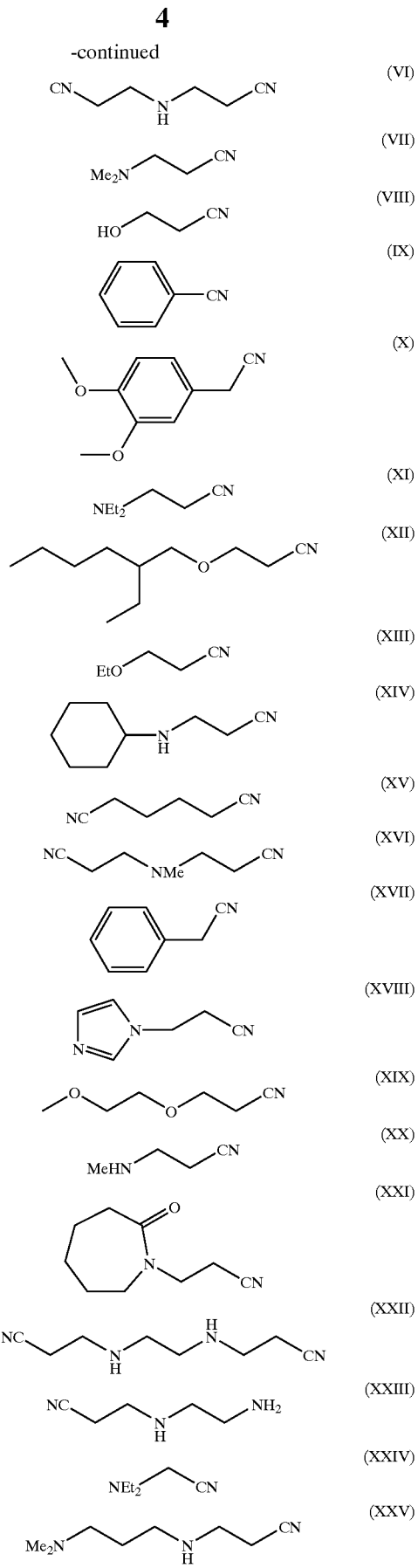

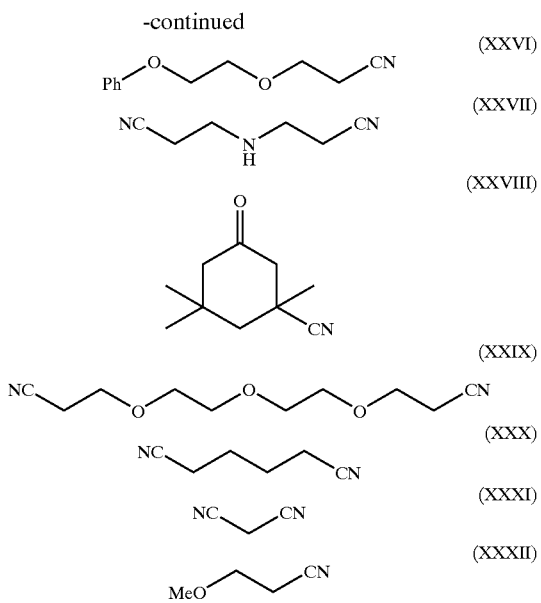

The hydrogenation is carried out continuously using a suspended catalyst which is in upward and downward fluidized motion. Dinitriles or polynitriles can also be partially hydrogenated. Altering the residence time enables the conversion and thus the product ratios of amines to aminonitriles to be set in a targeted manner.

The hydrogenation is carried out using a suspended catalyst. Suitable reactors for hydrogenation in the suspension mode are stirred vessels, jet loop reactors or bubble columns. The temperature is generally from 25 to 125° C., and the hydrogen pressure is generally from 10 to 300 bar. The nitrites to be hydrogenated may be present as a solution in an organic solvent. Preferred organic solvents are aliphatic alcohols, amines, amides such as N-methylpyrrolidone and dimethylformamide, ethers and esters. The space velocity over the catalyst is generally from 0.5 to 20, preferably from 2 to 10, mol of nitrile/$l_{catalyst}$*h.

The invention is illustrated by the following example.

EXAMPLE 10 g of Raney cobalt doped with nickel and chromium (Raney® 2724 from Grace Davison, Chattanooga, Tenn., USA) are placed in a continuously operated laboratory apparatus (150 ml autoclave provided with frit and double blade stirrer). The catalyst comprises 97.1% by weight of Co, 3.3% by weight of Al, 2.6% by weight of Ni, 2.1% by weight of Cr and 0.3% by weight of Fe. The reactor is subsequently flooded with dimethylformamide, heated to 100° C., and a 20% strength by weight solution of iminodiacetonitrile in dimethylformamide is hydrogenated by means of 20 standard l/h of hydrogen at 190 bar at WHSV over the catalyst of 0.15 kg/l (catalyst) *h. At a conversion of 100%, diethylenetriamine was formed with a selectivity of 82%.

We claim:

1. A process for the continuous hydrogenation of nitrites to primary amines in the liquid phase over a suspended, activated Raney catalyst based on an alloy of aluminum and at least one transition metal selected from the group consisting of iron, cobalt and nickel, and, if desired, one or more further transition metals selected from the group consisting of titanium, zirconium, chromium and manganese, wherein the hydrogenation is carried out in the absence of ammonia and basic alkali metal compounds or alkaline earth metal compounds.

2. A process as claimed in claim 1, wherein the catalyst has been produced on the basis of an alloy of aluminum and a solid solution of nickel in cobalt or of cobalt in nickel which comprises 0.05–50% by weight of the dissolved metal and, if desired, from 0.05 to 5% by weight of one or more of the further transition metals.

3. A process as claimed in claim 2, wherein the catalyst is activated by (a) treatment with aqueous alkali metal hydroxide solution, (b) rinsing the catalyst with aqueous alkali metal hydroxide solution and (c) rinsing the catalyst with water.

4. A process as claimed in claim 1, wherein the nitrile to be hydrogenated is present as a solution in an organic solvent.

5. A process as claimed in claim 4, wherein the organic solvent is dimethylformamide or N-methylpyrrolidone.

6. A process as claimed in claim 1, wherein the hydrogenation is carried out at from 25 to 125° C. and a hydrogen pressure of from 10 to 300 bar.

7. A process as claimed in claim 1, wherein the hydrogenation is carried out in a stirred vessel, a jet loop reactor or a bubble column.

8. A process as claimed in claim 1, wherein the nitrile is selected from the group consisting of extender nitrites and Michael adducts of acrylonitrile.

9. A process as claimed in claim 1, wherein the nitrile is selected from the group consisting of iminodiacetonitrile, nitrilotriacetonitrile, ethylenediaminetetraacetonitrile, biscyanoethylpiperazine, dimethylaminopropionitrile, dimethylaminopropylaminopropionitrile, isophoronenitrilimine and methoxypropionitrile.

* * * * *

UNITED STATES PATENT AND TRADEMARK OFFICE
CERTIFICATE OF CORRECTION

PATENT NO. : 6,469,211 B2
DATED : October 22, 2002
INVENTOR(S) : Ansmann et al.

It is certified that error appears in the above-identified patent and that said Letters Patent is hereby corrected as shown below:

<u>Title page,</u>
Item [57], ABSTRACT,
Line 1, "nitrites" should be -- nitriles --.

<u>Column 6,</u>
Line 9, "nitrites" should be -- nitriles --.

Signed and Sealed this

Eighteenth Day of February, 2003

JAMES E. ROGAN
*Director of the United States Patent and Trademark Office*